United States Patent
Allen et al.

(10) Patent No.: US 7,182,910 B2
(45) Date of Patent: Feb. 27, 2007

(54) COLLECTION WELL FOR BODY FLUID TESTER

(75) Inventors: John J. Allen, Mendota Heights, MN (US); Joel R. Racchini, Edina, MN (US)

(73) Assignee: Integ, Inc., St. Paul, MN (US)

(*) Notice: Subject to any disclaimer, the term of this patent is extended or adjusted under 35 U.S.C. 154(b) by 116 days.

(21) Appl. No.: 10/611,824

(22) Filed: Jun. 30, 2003

(65) Prior Publication Data

US 2004/0096957 A1 May 20, 2004

Related U.S. Application Data

(63) Continuation of application No. 10/001,776, filed on Oct. 18, 2001, now Pat. No. 6,663,835, which is a continuation of application No. 09/513,013, filed on Feb. 25, 2000, now Pat. No. 6,375,626, which is a continuation-in-part of application No. 09/267,179, filed on Mar. 12, 1999, now Pat. No. 6,368,563.

(51) Int. Cl.
*G01N 21/01* (2006.01)
*G01N 31/20* (2006.01)
*A61B 5/151* (2006.01)

(52) U.S. Cl. .......................... 422/50; 422/55; 422/59; 422/58; 422/101; 600/573; 600/575; 600/576; 600/577; 604/289; 604/317; 604/324; 604/326; 436/180

(58) Field of Classification Search ............... 422/50, 422/55, 58, 59, 100, 102, 104; 600/573, 600/575, 576, 577, 578, 584; 604/289, 317, 604/324, 326; 436/180

See application file for complete search history.

(56) References Cited

U.S. PATENT DOCUMENTS

| 3,123,066 A | 3/1964 | Brumley |
| 3,136,310 A | 6/1964 | Meltzer |
| 3,208,452 A | 9/1965 | Stern |
| 3,338,239 A | 8/1967 | Mausteller |
| 3,958,560 A | 5/1976 | March |

(Continued)

FOREIGN PATENT DOCUMENTS

DE 3708031 11/1987

(Continued)

OTHER PUBLICATIONS

Pamphlet: "Glucometer Elite®", *Bayer Corporation*, (Mar. 1996).

(Continued)

*Primary Examiner*—Krishnan S. Menon
(74) *Attorney, Agent, or Firm*—Kagan Binder, PLLC

(57) ABSTRACT

A body fluid is collected for testing for an analyte contained within the body fluid. The fluid is collected in an apparatus including a reservoir for receiving and collecting a flow of body fluid from a discharge end of a conduit. A capillary test space is in fluid flow communication with the reservoir. The capillary test space is positioned to be in contact with the fluid in the reservoir after the fluid has accumulated to a predetermined transfer volume of fluid. The capillary test space is sized to wick the fluid from the reservoir when the fluid contacts the capillary test space.

12 Claims, 8 Drawing Sheets

U.S. PATENT DOCUMENTS

| | | |
|---|---|---|
| 4,014,321 A | 3/1977 | March |
| 4,081,779 A | 3/1978 | Ranzanigo |
| 4,195,641 A | 4/1980 | Joines et al. |
| 4,200,100 A | 4/1980 | Willis |
| 4,407,290 A | 10/1983 | Wilber |
| 4,489,974 A | 12/1984 | Warhol |
| 4,517,978 A | 5/1985 | Levin et al. |
| 4,545,382 A | 10/1985 | Higgins et al. |
| 4,622,974 A | 11/1986 | Coleman et al. |
| 4,627,445 A | 12/1986 | Garcia et al. |
| 4,637,403 A | 1/1987 | Garcia et al. |
| 4,648,408 A | 3/1987 | Hutcheson et al. |
| 4,655,225 A | 4/1987 | Dahne et al. |
| 4,658,825 A | 4/1987 | Hochberg et al. |
| 4,660,971 A | 4/1987 | Sage et al. |
| 4,664,128 A | 5/1987 | Lee |
| 4,685,463 A | 8/1987 | Williams |
| 4,703,756 A | 11/1987 | Gough et al. |
| 4,704,029 A | 11/1987 | Van Heuvelen |
| 4,730,622 A | 3/1988 | Cohen |
| 4,750,830 A | 6/1988 | Lee |
| 4,766,908 A | 8/1988 | Clement |
| 4,805,623 A | 2/1989 | Jobsis |
| 4,873,993 A | 10/1989 | Meserol et al. |
| 4,882,492 A | 11/1989 | Schlager |
| 4,883,068 A | 11/1989 | Dechow |
| 4,901,728 A | 2/1990 | Hutchison |
| 4,953,552 A | 9/1990 | DeMarzo |
| 4,954,318 A | 9/1990 | Yafuso et al. |
| 4,960,467 A | 10/1990 | Peck |
| 4,981,779 A | 1/1991 | Wagner |
| 4,995,402 A | 2/1991 | Smith et al. |
| 5,002,054 A | 3/1991 | Ash et al. |
| 5,014,718 A | 5/1991 | Mitchen |
| 5,026,388 A | 6/1991 | Ingalz |
| 5,029,583 A | 7/1991 | Meserol et al. |
| 5,035,704 A | 7/1991 | Lambert et al. |
| 5,036,861 A | 8/1991 | Sembrowich et al. |
| 5,046,508 A | 9/1991 | Weissler |
| 5,049,487 A | 9/1991 | Phillips et al. |
| 5,054,499 A | 10/1991 | Swierczek |
| 5,066,859 A | 11/1991 | Karkar et al. |
| 5,070,886 A | 12/1991 | Mitchen |
| 5,079,421 A | 1/1992 | Knudson et al. |
| 5,100,620 A | 3/1992 | Brenneman |
| 5,115,133 A | 5/1992 | Knudson |
| 5,139,023 A | 8/1992 | Stanley et al. |
| 5,146,091 A | 9/1992 | Knudson |
| 5,165,419 A | 11/1992 | Sarstedt |
| 5,179,951 A | 1/1993 | Knudson |
| 5,201,324 A | 4/1993 | Swierczek |
| 5,203,327 A | 4/1993 | Schoendorfer et al. |
| 5,203,504 A | 4/1993 | Frost et al. |
| 5,222,496 A | 6/1993 | Clarke et al. |
| 5,231,993 A | 8/1993 | Haber et al. |
| 5,250,439 A | 10/1993 | Musho et al. |
| 5,266,179 A | 11/1993 | Nankai et al. |
| 5,320,607 A | 6/1994 | Ishibashi |
| 5,362,445 A | 11/1994 | Miyahara et al. |
| 5,368,047 A | 11/1994 | Suzuki et al. |
| 5,397,537 A | 3/1995 | Kanda et al. |
| 5,437,841 A | 8/1995 | Balmer |
| 5,443,080 A | 8/1995 | D'Angelo et al. |
| 5,453,360 A | 9/1995 | Yu |
| 5,458,140 A | 10/1995 | Eppstein et al. |
| 5,470,757 A | 11/1995 | Gagnon et al. |
| 5,508,171 A | 4/1996 | Walling et al. |
| 5,582,184 A | 12/1996 | Erickson et al. |
| 5,628,890 A | 5/1997 | Carter et al. |
| 5,682,233 A | 10/1997 | Brinda |
| 5,700,695 A | 12/1997 | Yassinzadah et al. |
| 5,746,217 A | 5/1998 | Erickson et al. |
| 5,810,985 A | 9/1998 | Bao et al. |
| 5,820,570 A | 10/1998 | Erickson et al. |
| 5,823,973 A | 10/1998 | Racchini et al. |
| 5,879,310 A | 3/1999 | Sopp et al. |
| 5,879,367 A | 3/1999 | Latterell et al. |
| 5,964,718 A | 10/1999 | Duchon et al. |
| 5,984,695 A | 11/1999 | Riehl et al. |
| 6,001,239 A | 12/1999 | Douglas et al. |
| 6,009,632 A | 1/2000 | Douglas |
| 6,015,392 A | 1/2000 | Douglas et al. |
| 6,028,311 A | 2/2000 | Sodickson et al. |
| 6,054,277 A | 4/2000 | Furcht et al. |
| 6,080,116 A | 6/2000 | Erickson et al. |
| 6,152,889 A | 11/2000 | Sopp et al. |
| 6,203,504 B1 | 3/2001 | Latterell et al. |
| 6,368,563 B1 | 4/2002 | Allen et al. |
| 6,375,626 B1 | 4/2002 | Allen et al. |
| 6,602,205 B1 | 8/2003 | Erickson et al. |
| 6,614,522 B1 | 9/2003 | Sopp et al. |
| 6,624,882 B2 | 9/2003 | Sopp et al. |
| 6,712,776 B2 | 3/2004 | Latterell et al. |

FOREIGN PATENT DOCUMENTS

| | | |
|---|---|---|
| EP | 0 160 768 | 11/1985 |
| EP | 0 199 484 | 10/1986 |
| EP | 0 212 906 | 3/1987 |
| EP | 0 250 257 | 12/1987 |
| EP | 0 306 158 A2 | 3/1989 |
| EP | 0 396 016 A2 | 11/1990 |
| EP | 0 453 283 | 10/1991 |
| EP | 0 555 554 | 8/1993 |
| EP | 0 582 226 | 2/1994 |
| EP | 0 864 363 A2 | 12/1997 |
| GB | 2033575 | 5/1980 |
| JP | 10-104192 | 4/1998 |
| WO | WO 85/04089 | 9/1985 |
| WO | WO 88/00812 | 2/1988 |
| WO | WO 91/18548 | 12/1991 |
| WO | WO 92/11879 | 7/1992 |
| WO | WO 93/00043 | 1/1993 |
| WO | WO 95/10223 | 4/1995 |
| WO | WO 97/38126 | 10/1997 |
| WO | WO 97/42883 | 11/1997 |

OTHER PUBLICATIONS

User Guide: "Glucometer Elite®", *Bayer Corporation*, (Dec. 1996).
Arnold, M., et al., "Determination of Physiological Levels of Glucose in an Aqueous Matrix with Digitally Filtered Fourier Transform Near-Infrared Spectra," *Analytical Chemistry*, vol. 63, No. 14, pp. 1457-1464 (Jul. 1990).
Ash, S., et al., "Subcutaneous Capillary Filtrate Collector for Measurement of Blood Chemistries" *ASAIO Journal*, vol. 38, pp. M416-M420 (1992).
Ash, S., et al., :A Subcutaneous Capillary Filtrate Collector for Measurement of Blood Chemistries, *ASAIO Journal*, vol. 39, No. 3, pp. M699-M704 (1993).
Bruce, R., et al., "Reevaluation of the Needle Method for Measuring Interstitial Fluid Pressure," *American Journal of Physiology*, vol. 229, No. 3, pp. 603-607 (Sep.1975).
DuPuy, N., et al., "Quantitative Analysis of Aqueous Solutions by FTIR Spectroscopy of Dry-Extract," *SPIE*, vol. 1575, 8th International Conference on Fourier Transform Spectroscopy, pp. 501-502 (1991).
Geiman Science Brochure, showing Nylaflo Catalog P/N 332378, p. 60 (1993).
Gilanyi, M., et al., "Ion Concentrations In Subcutaneous Interstitial Fluid: Measured Versus Expected Values," *Am. J. Physiol.*, vol. 255, No. 3 (pt. 2), pp. F513-F519 (Sep. 1988).
Ginsberg, B., "An Overview of Minimally Invasive Technologies," *Clinical Chemistry*, vol. 38, No. 9, pp. 1596-1600 (1992).

"Glucose Sensors" and "Like an Injection" sections on p. 26 of Diabetes forecast (May 1993).

Janle-Swain, E., et al., "Use of a Capillary Filtrate Collector for Monitoring Glucose in Diabetics," *Trans.Am.Soc.Artif.Intern.Organs*, vol. XXXIII, pp. 336-340 (1987).

Kayashima, S., et al., "New Noninvasive Transcutaneous Approach to Blood Glucose Monitoring on Human 75 g OGTT with Novel Sampling Chamber," *IEEE Transactions on Biomedical Engineering*, vol. 38, No. 8, pp. 752-757 (Aug. 1991).

Kayashima, S., et al., "Suction Effusion Fluid from Skin and Constituent Analysis: New Candidate for Interstitial Fluid," *Am. J. Physiol.*, vol. 263, No. 5 (Pt. 2), pp. H1623-H1627 (Nov. 1992).

Kiistala, U., "Suction Blister Device for Separation of Viable Epidermis from Dermis," *Journal of Investigative Dermatology*, vol. 50, No. 2, pp. 129-137 (1968).

Korthuis, R., et al., "Methods for Sampling Interstitial Fluid," from book entitled *Microcirculatory Technology*, edited by C.H. Baker, et al, Academic Press, Chapter 21, pp. 326-327 (1986).

Mendelson, Y., et al., "Blood Glucose measurement by Multiple Attenuated Total Reflection and Infrared Absorption Spectroscopy," *IEEE Transactions on Biomedical Engineering*, vol. 37, No. 5, pp. 458-465 (May 1990).

Moatti-Sirat, D., et al., "Towards Continuous Glucose Monitoring: In Vivo Evaluation of a Miniaturized Glucose Sensor Implanted for Several Days in Rat Subcutaneous Tissue," *Diabetologia*, vol. 35, No. 3, pp. 224-230 (Mar. 1992).

Petersen, L., et al., "Microdialysis of the Interstitial Water Space in Human Skin In Vivo: Quantitative Measurement of Cutaenous Glucose Concentrations," *Journal of Investigative Dermatology*, vol. 99, No. 3, pp. 357-360 (Sep. 1992).

Turner, A., et al., "Diabetes Mellitus: Biosensors for Research and Management," *Biosensors*, vol. 1, pp. 85-115 (1985).

Wiig, H., "Evaluation of Methodologies for Measurement of Interstitial Fluid Pressure ($P_i$): Physiological Implications of Recent $P_i$ Data," *Crit.Rev.in Biomed.Eng.*, vol. 18, No. 1, pp. 27-54 (1990).

Wolfson, Jr., S., et al., "Glucose Concentration at Possible Sensor Tissue Implant Sites," *Diabets Care*, vol. 5, No. 3, pp. 162-165 (May/Jun. 1982).

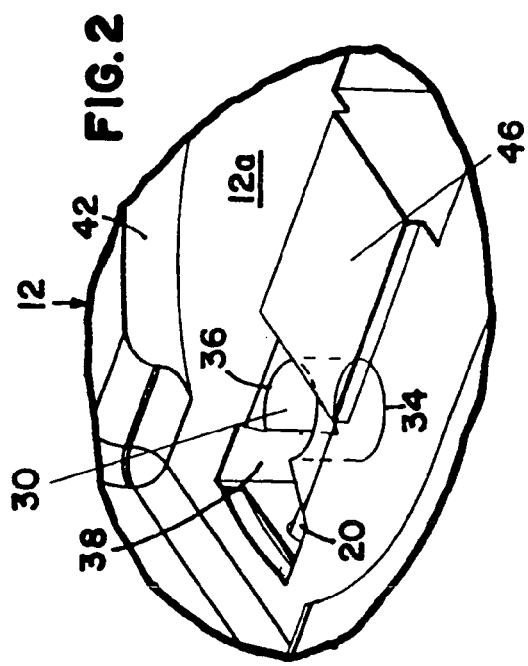
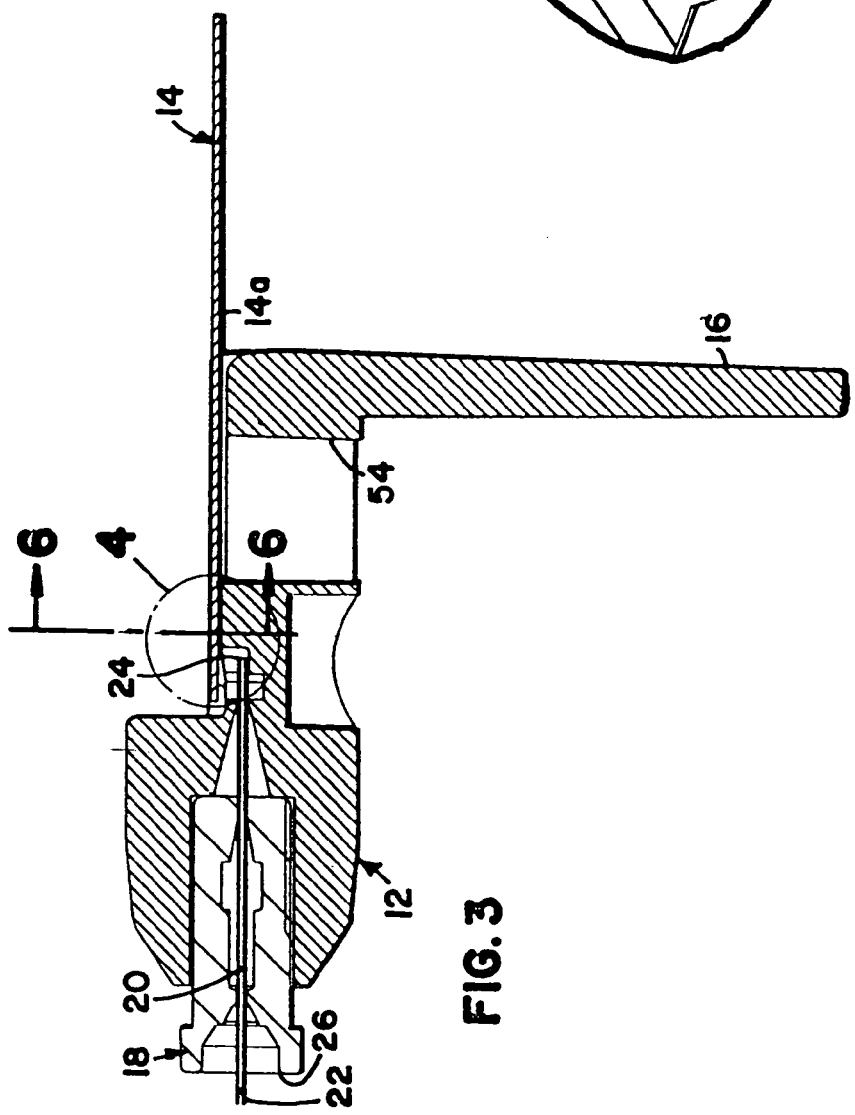

FIG. 11
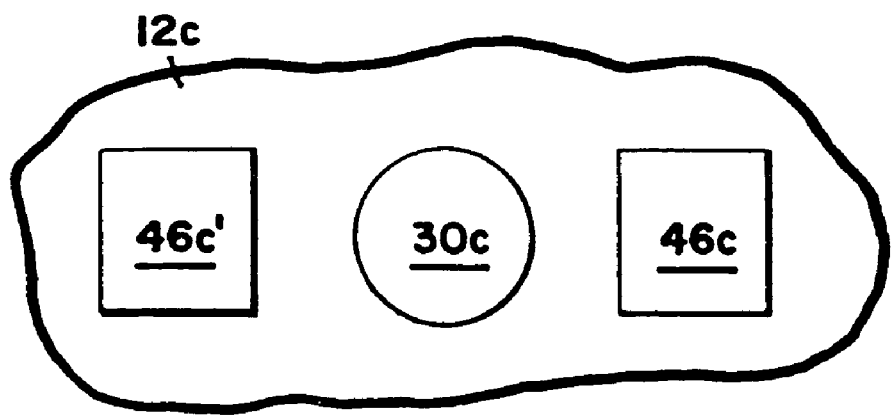
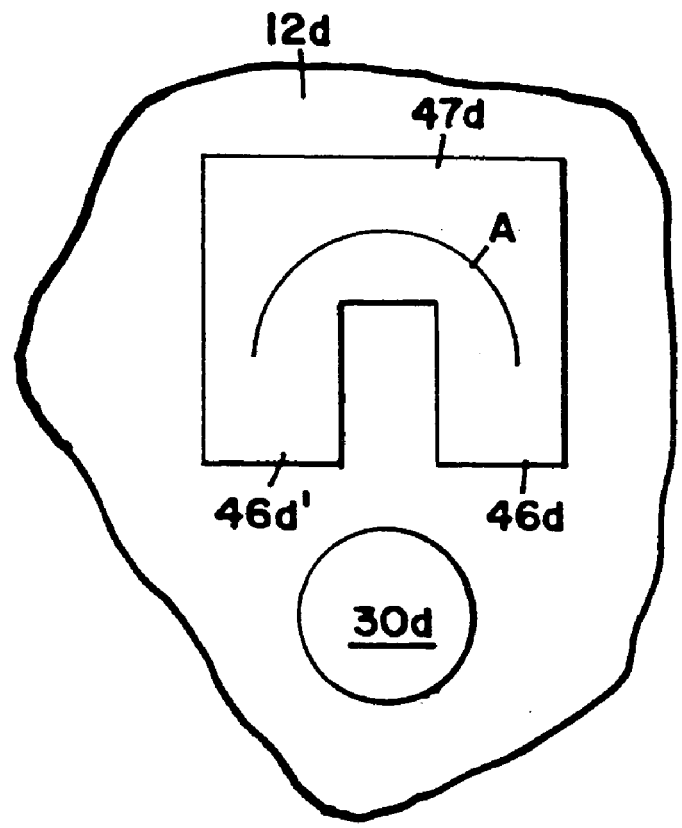
FIG. 12

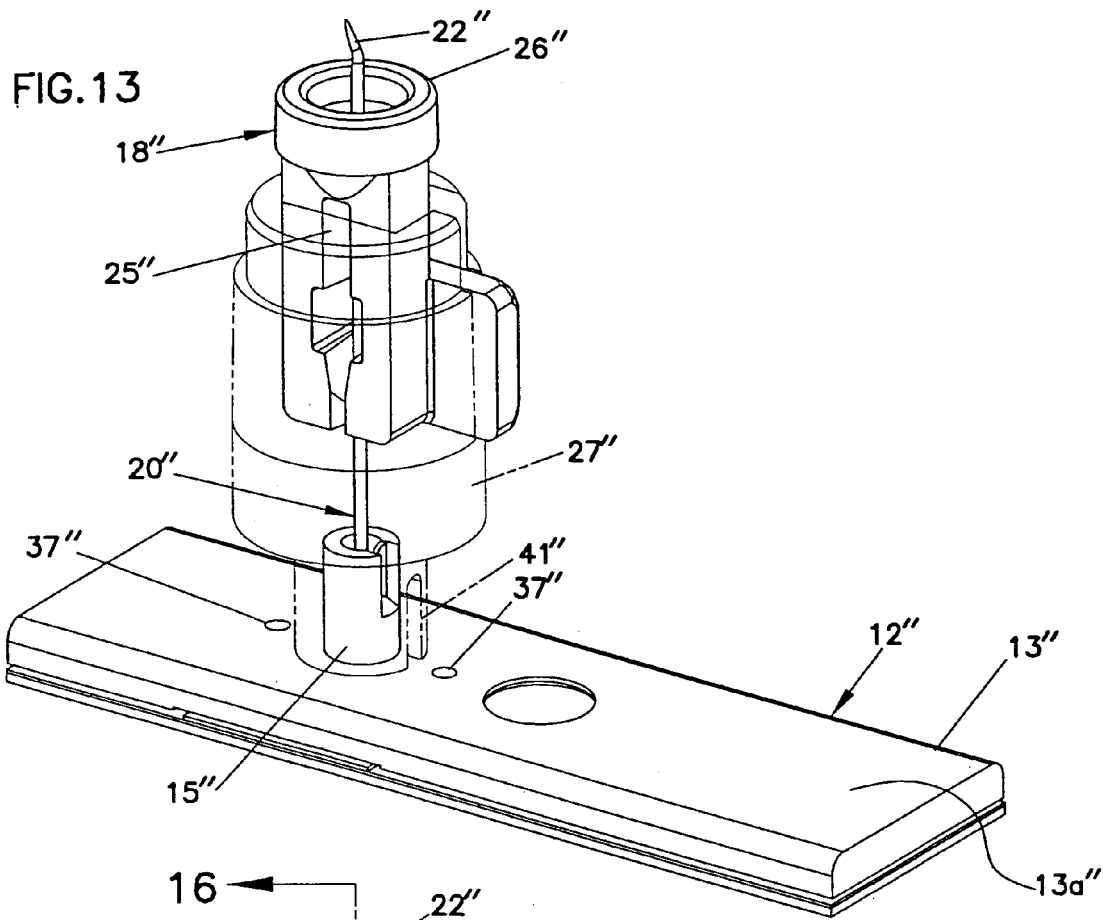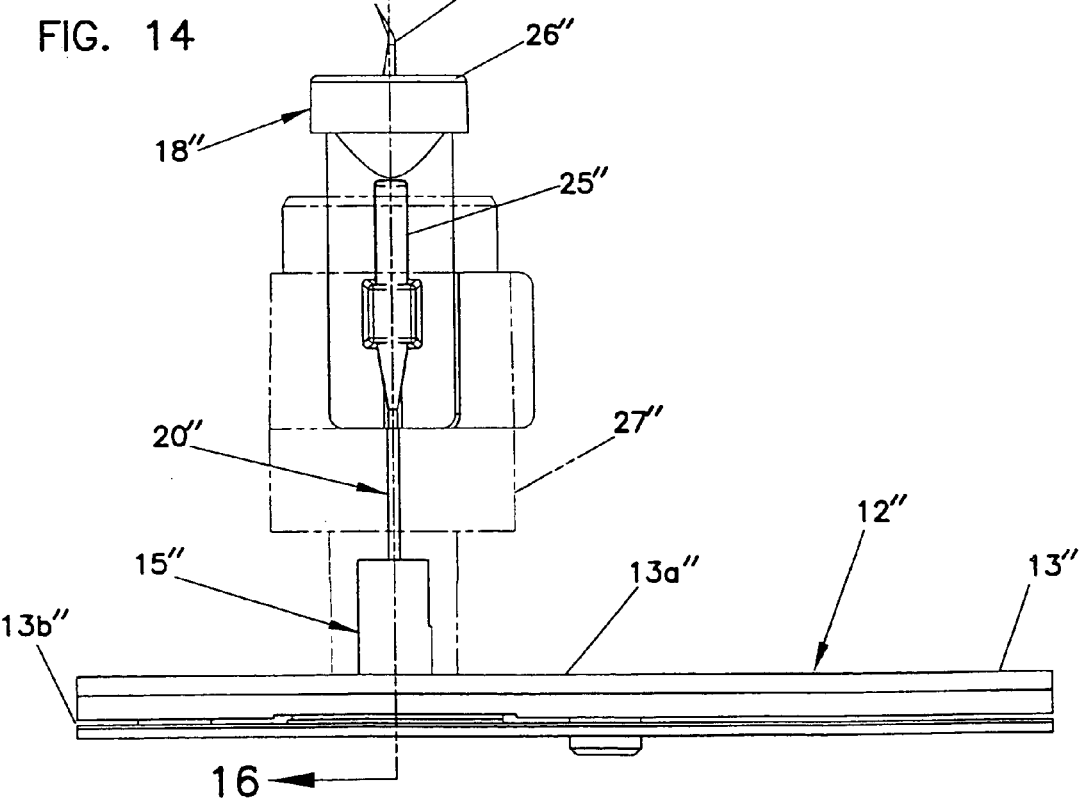

COLLECTION WELL FOR BODY FLUID TESTER

CROSS-REFERENCES

This application is a continuation of application Ser. No. 10/001,776, filed Oct. 18, 2001 (now U.S. Pat. No. 6,663, 835, issued Dec. 16, 2003) which is a continuation of application Ser. No. 09/513,013, filed Feb. 25, 2000 (now U.S. Pat. No. 6,375,626, issued Apr. 23, 2002) which is a continuation-in-part of application Ser. No. 09/267,179, filed Mar. 12, 1999 (now U.S. Pat. No. 6,368,563, issued Apr. 9, 2002) all of which are incorporated herein by reference.

TECHNICAL FIELD

This invention pertains to testing a body fluid for an analyte. For example, the present invention is applicable for testing glucose in a body fluid such as blood or interstitial fluid.

BACKGROUND

Numerous patents teach various ways for collecting a sample of body fluid and testing such fluid for an analyte such as glucose. For example, U.S. Pat. Nos. 5,823,973 and 5,820,570 describe methods and apparatus for obtaining, in one embodiment, interstitial fluid, which is tested for glucose through IR absorption. These patents also describe use of the disclosed inventions in colormetric and electro-chemical testing of glucose. U.S. Pat. No. 5,453,360 teaches a test strip for colormetric testing for glucose. Blood is placed on a test strip containing various chemical components including a dye. The degree of color change of the test strip indicates the amount of glucose. U.S. Pat. Nos. 5,508, 171 and 5,628,890 teach electro-chemical testing. Blood is placed on a test strip containing electrodes. Reaction of glucose on the electrodes generates a current indicating the amount of glucose present in the blood.

Present development efforts are directed to testing very small volumes of body fluid (e.g. about 0.5 microliter). The use of such small volumes of fluid permits less painful collection of a fluid samples. However, small fluid volumes present additional challenges for analyte testing. For example, testing for analytes typically requires a fluid sample in excess of a predetermined minimum volume. By way of non-limiting representative example, a test may require a minimum sample size of 5 microliter to yield reliable test results.

Furthermore, sample collection systems may receive a flow of body fluid over an extended time (e.g., 10 seconds or more) before a minimum sample volume is collected. As a result, body fluid may be deposited on test components (e.g., electrodes or colormetric test strips) before a full sample is collected. Such premature deposit may initiate chemical reactions on a test strip thereby consuming reagents before a reliable test can be initiated. Further, such test components may be coupled to logic circuits for calculating an analyte's concentration based on readings from the test strip. A premature deposit of an inadequate volume of fluid sample may falsely inform logic circuits that testing has initiated when, in fact, an adequate sample volume has yet to be collected.

Recognizing the problems of premature test initiation, the prior art has developed techniques for delaying test initiation until an adequate volume of sample is collected. For example, logic circuits may have a built-in time delay which assumes a fixed period of time to collect an adequate volume of sample. Of course, such systems suffer from the fact there is no certainty that an adequate volume is collected during such time delay. Alternatively, to be conservative, such time delays may frequently be unnecessarily long. Additionally, U.S. Pat. No. 5,049,487 teaches reading a reflectance of a side of a membrane. A fluid sample is placed on the opposite side. When the sample is absorbed through the membrane, the change in reflectance is noted indicating testing may commence. However, such a system suffers from chemical agents on the membrane being in contact with a sample prior to initiating testing.

Therefore, there is a need for a method and apparatus for collecting a sample of body fluid to obtain an adequate volume of such fluid.

SUMMARY

According to a preferred embodiment of the present invention, a method and apparatus are disclose for collecting a body fluid for testing for an analyte contained within the body fluid. The apparatus includes a reservoir for receiving and collecting a flow of body fluid from a discharge end of a conduit. A capillary test space is in fluid flow communication with the reservoir. The capillary test space is positioned to be in contact with the fluid in the reservoir after the fluid has accumulated to a predetermined transfer volume of fluid. The capillary test space is sized to wick the fluid from the reservoir when the fluid contacts the entrance end. With the present invention, fluid is collected within the reservoir at a rate of flow limited by the conduit. When the reservoir is full, the collected fluid rapidly wicks into the capillary test space. The capillary test space may contain test components for testing for the analyte.

BRIEF DESCRIPTION OF THE DRAWINGS

FIG. 2 is an enlarged segmented view of the area of circle 2 in FIG. 1;

FIG. 3 is a side-sectional view of the apparatus of FIG. 1 showing the test strip in place;

FIG. 11 is a top plan view of the embodiment of FIG. 10 with a test strip removed;

FIG. 12 is a view similar to FIG. 11 showing a fourth alternative embodiment of the present invention;

FIG. 13 is a bottom, rear end and right side perspective view of a still further embodiment of a sample collection apparatus according to the present invention;

FIG. 14 is a right side elevation view of the apparatus of FIG. 13;

DETAILED DESCRIPTION

Figure 1:
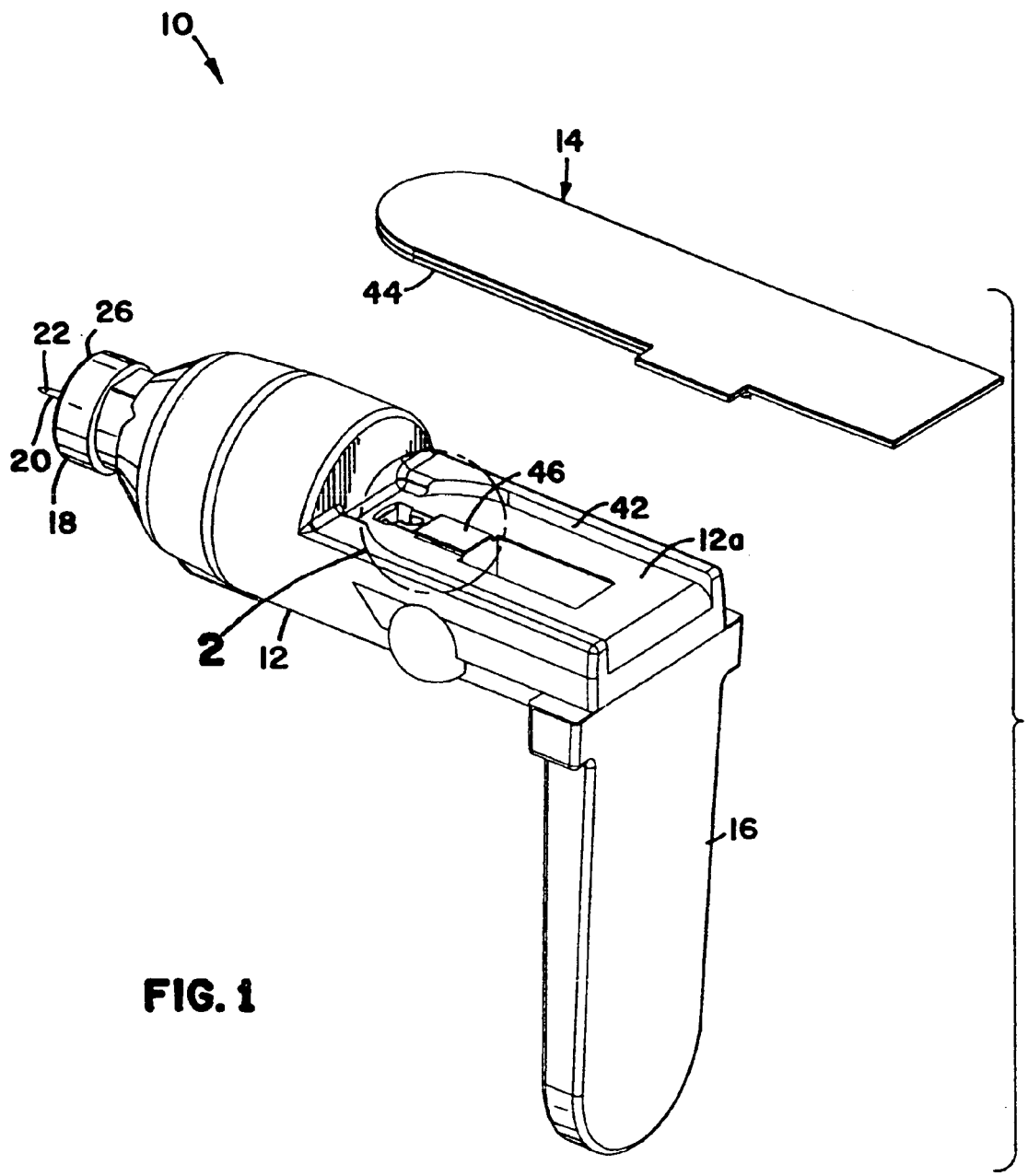
FIG. 1 is a perspective view of a sample collection apparatus with an electro-chemical test strip shown removed.

With reference to the various drawing figures in which identical elements are numbered identically throughout, a description of a preferred embodiment will now be provided. Throughout this description, the present invention will be described with reference to collecting a sample of interstitial fluid for glucose testing using a narrow needle that penetrates into, but not through, the dermis as more fully described in commonly assigned U.S. Pat. Nos. 5,823,973 and 5,820,570, the disclosures for both of which are hereby incorporated herein by reference. While such a use is a preferred embodiment, the present invention is applicable to other fluid collection systems (e.g., blood collection) as well as testing for other fluid analytes. Further, the present invention is described with reference to using electro-chemical testing of a collected sample. The teachings of the present invention are equally applicable to other testing methods such as colormetric testing and IR absorption testing.

Referring now to FIGS. 1–6, a collection apparatus 10 includes a main body 12 and a test strip 14. The main body has a handle 16 and a needle-containing ferrule 18. The ferrule 18 holds a hollow needle 20 extending from a penetration end 22 to a discharge end 24. The penetration end 22 protrudes from a radially spaced ring end 26 of the ferrule 18.

In a preferred embodiment, the penetration end 22 is axially spaced from ring end 26 by a distance sufficient for the needle 20 to penetrate into but not through a patient's dermis to collect a sample of substantially blood-free interstitial fluid as taught in U.S. Pat. No. 5,820,570. In such an embodiment, the outer diameter of the needle is about 0.013 inch (about 0.33 mm). This sizing of the needle permits substantially pain-free penetration of the needle to collect a body fluid. This description illustrates a preferred embodiment. Needle 20 may be sized to collect any body fluid such as blood or interstitial fluid. Further, the present invention is disclosed where the skin penetration member (i.e., the needle 20) also serves as a conduit for supplying fluid to a reservoir 30 as will be described. The present invention is also applicable to any conduit for transporting a body fluid (e.g., a capillary tube as described in International Application PCT/US97/08400 published Nov. 20, 1997 as International Publication No. WO 97/42883).

The test strip 14 contains exposed test components on an inner surface 14a. The test components are shown in the form of electrodes 32 for testing a body fluid for an analyte such as glucose through electrochemical testing. As previously described, the test components could be components for alternate testing techniques such as colormetric or IR absorption testing.

Not shown is a housing for holding the apparatus 10 during sample collection and testing. Housings for holding disposable body fluid samplers are shown in U.S. Pat. No. 5,823,973. Such housings may contain electrical components for electrical connection to the test strip electrodes 32 to connect a signal from the electrodes 32 to logic circuits to compute and report on the analyte in response to signals from the electrodes 32 during testing.

The material of the main body 12 defines a cylindrical reservoir 30 having a cylindrical axis between a first end 34 and a second end 36. In the embodiment shown, the axis of the reservoir 30 is perpendicular to the axis of the needle 20. Such a relative alignment is not necessary for adequate function and any other alignment is acceptable.

The reservoir 30 has a volume at least as great as a desired test volume of body fluid to be tested. In a preferred embodiment, reservoir 30 has a volume of 0.7 microliters. As will become apparent, fluid is collected in the reservoir 30 and accumulates with a fluid level rising from the first end 34 toward the second end 36. Due to such small volumes and the geometry of reservoir 30, surface tension assures the fluid is retained in the reservoir 30 with the fluid level rising as described regardless of the orientation of the apparatus 10 (i.e., the operation of the apparatus 10 is gravity independent).

The discharge end 24 of the needle 20 is disposed within the reservoir 30 adjacent the first end 34. Accordingly, body fluid is transported from the penetration end 22, through needle 20 and discharged from the discharge end 24 into the reservoir 30 at the first end 34.

The material of the body 12 also defines an enlarged empty volume 38 positioned between the reservoir 30 and the ferrule 18 and surrounding the needle 20. The enlarged volume 38 is separated from the reservoir 30 by material of the main body pinching against the needle 20 as at locations 40. The enlarged volume 38 has a volume larger than the reservoir 30 and ensures that fluid within the reservoir 30 is retained within reservoir 30 as it accumulates. For example, in the absence of enlarged volume 38, manufacturing tolerances may result in a narrow spacing between the material of main body 12 and needle 20. Such a narrow spacing could function as a capillary space communicating with reservoir 30 which would wick fluid out of reservoir 30. The enlarged volume 38 precludes such capillary wicking. Further, the material defining the volume 38 is preferably hydrophobic to minimize wicking. In the event precise manufacturing permits complete liquid-tight sealing around needle 20, the enlarged volume 38 could be eliminated.

The test strip 14 is secured to the main body (e.g., through adhesives) with the inner surface 14a facing the main body 12 and overlying the second end 36 of the reservoir 30. The main body 12 includes a groove 42 shaped complementary to the outer periphery of the test strip 14 to ensure accurate alignment of the test strip 14 with the main body 12. Adjacent its outer periphery, the inner surface 14a of the test strip 14 includes spacers 44 (shown best in FIG. 6). The spacers 44 insure uniform and close parallel spacing of the inner surface 14a from a test strip opposing surface 12a of the main body 12 for reasons that will become apparent. Alternatively, spacers could be formed on the body 12 thereby eliminating the need for spacers 44.

Figure 6:
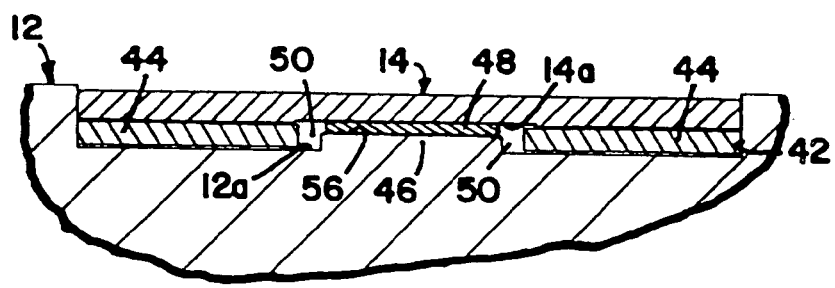
FIG. 6 is a view taken along line 6—6 in FIG. 3 and showing a bolus of body fluid residing in a capillary test space.

The test strip opposing surface 12a includes a step 46. With reference to FIG. 6, the construction described above results in formation of a capillary test space 48 defined between opposing surfaces of the test strip inner surface 14a and step 46.

As shown in FIG. 6, the spacers 44 are spaced from opposing surfaces of the step 46 thereby defining enlarged volumes 50 on opposite sides of the step 46. The enlarged volumes 50 perform a function similar to that of enlarged volume 38. Namely, if the spacers 44 were sized to abut step 46, small capillary spaces could form between the spacers 44 and step 46. Such capillary spaces could wick fluid from the fluid receiving volume 48. Again, if manufacturing could ensure a fluid-tight seal between spacers 44 and step 46, the volumes 50 could be eliminated.

Figure 4:
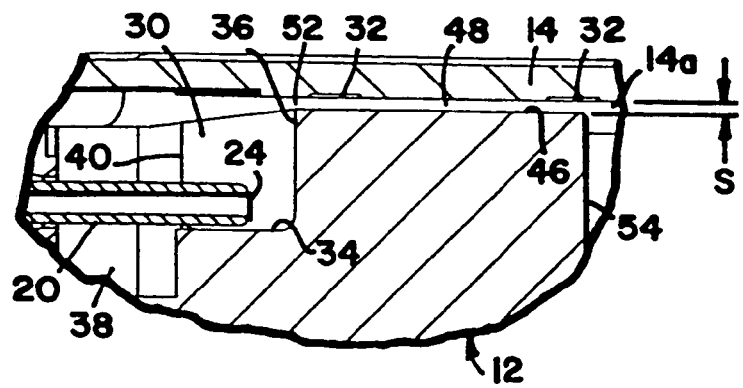
FIG. 4 is an enlarged segmented view of the area of circle 4 in FIG. 3.
Figure 5:
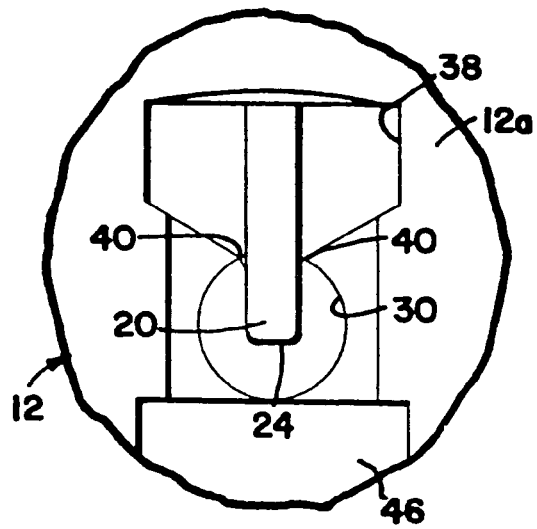
FIG. 5 is a segmented top-plan view of a reservoir of the apparatus of FIG. 1.

Shown best in FIGS. 4 and 6, the electrodes 32 are positioned opposing the step 46. Further, the spacing S (FIG. 4) between the step 46 and inner surface 14a is uniform and is selected to be sufficiently narrow for the capillary test space 48 to act as a capillary space to wick fluid from the reservoir 30. An entrance end 52 of the capillary test space 48 is positioned at the second end 36 of the reservoir 30 (FIG. 4). The preferred spacing S is about 0.003–0.005 inch (about 0.075 mm to 0.125 mm). The spacing S may be as large as 0.012 inch (about 0.300 mm) or larger depending. on the surface tension and volume of the fluid being collected and the relative hydrophobic/hydrophilic characteristics of the main body 12 and test strip 14.

A hole 54 is formed through the body 12 and into the fluid receiving volume 48 on a side of the step 46 opposite the reservoir 30. The hole 54 permits air in the capillary test space 48 to be vented to atmosphere as fluid flows into the capillary test space 48 from the reservoir 30. Volumes 50 also provide venting.

With the construction thus described, the apparatus 10 is used by urging the ring end 26 against a patient's skin. The penetration tip 22 penetrates the skin. The ring end 26 (being radially spaced from tip 22) acts to urge fluid into the needle 20. The fluid flows along the needle 20 and discharges into the first end 34 of the reservoir 30 through discharge end 24. In one possible embodiment, suction could be applied to advance the rate of flow of fluid through needle 20. Suction is not used in other embodiments.

Fluid accumulates in the reservoir 30 with a level of accumulated fluid growing from the first end 34 to the second end 36. When the fluid level reaches the second end 36, a desired volume of fluid to be tested has accumulated in the reservoir 30. At this time, the fluid level contacts the entrance end 52 of the capillary test space 48. Since the capillary test space 48 is a narrow capillary space, the fluid is rapidly wicked out of the reservoir 30 and into the capillary test space 48 as a bolus delivery of fluid indicated by the bolus of fluid 56 in FIG. 6. So positioned, the fluid is in contact with the electrodes 32 and testing of the fluid may commence.

The present invention permits fluid contact with the electrodes 32 only after an adequate volume of fluid has been collected. By way of non-limiting representative example, it may take thirty seconds for fluid to fill the reservoir 30 and only one second for the accumulated fluid to be wicked into the capillary test space 48 from the reservoir 30. As a result, the present invention avoids a long period of time during which fluid is contacting the electrodes 32 and before testing may commence. Further, without the need for specialized electronics as used in the prior art, testing cannot commence until after an adequate volume of fluid has been accumulated. Therefore, when a signal is received from electrodes 32, it is known that an adequate volume of fluid is opposing the electrodes 32.

The retention of fluid in the reservoir 30 and wicking of fluid into the capillary test space 48 can be controlled and modified by varying the dimensions of the components as will be apparent to one of ordinary skill in the art having the benefit of the teachings of the present invention. Further, as will be apparent to such artisan, such retention and wicking may also be controlled and modified through material selection. For example, it is desirable that the main body 12 be formed of hydrophobic material and that the capillary test space 48 be more hydrophilic. For example, a hydrophilic surfactant may be applied to step 46 or test strip inner surface 14a (or both) to make the capillary test space 48 more hydrophilic than the reservoir 30.

It may be desirable to have one of electrodes 32 completely wetted with fluid from reservoir 30 before the other of the electrodes 30 is wetted. FIGS. 7–12 illustrate several alternative embodiments for achieving such sequential wetting. In the embodiments, elements in common with those already described are numbered identically with the addition of letter suffixes (i.e., "a", "b", "c" and "d"). Such elements are not separately described unless modified by the alternative embodiment.

Figure 7:
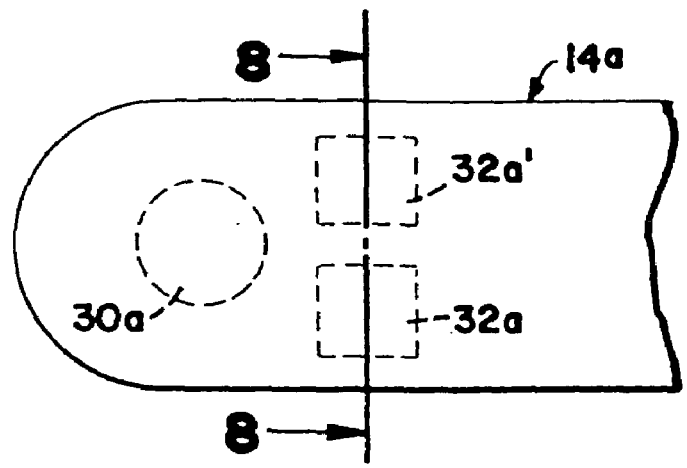
FIG. 7 is a top plan view of a first alternative embodiment of the present invention.
Figure 8:
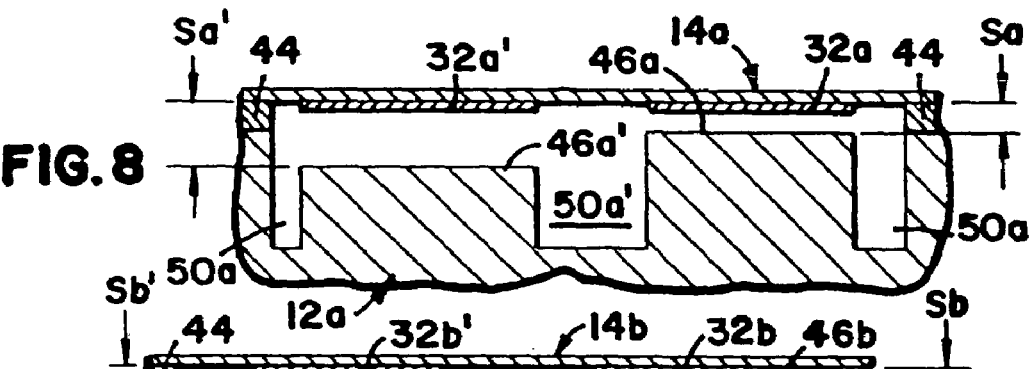
FIG. 8 is a view taken along line 8—8 of FIG. 7.

In FIGS. 7 and 8, it is desirable to completely wet electrode 32a before wetting electrode 32a'. The electrodes 32a, 32a' are positioned side-by-side on test strip 14a and equidistant from reservoir 30a. As shown in FIG. 8, the step 46 of the previously described embodiment is divided into two steps 46a, 46a' opposing respective ones of electrodes 32a, 32a'. A hydrophobic volume 50a' is positioned between the steps 46a, 46a'. The volume 50a' functions similarly to side volumes 50a (and 50 in the embodiment of FIG. 6) to act as a hydrophobic barrier to prevent fluid from flowing between the steps 46a, 46a'. The steps 46a, 46a' are spaced from test strip 14 by spaces Sa and Sa'. Since space Sa is smaller than space Sa', fluid first flows from reservoir 30a into space Sa before flowing from reservoir 30a into space Sa'.

Figure 9:
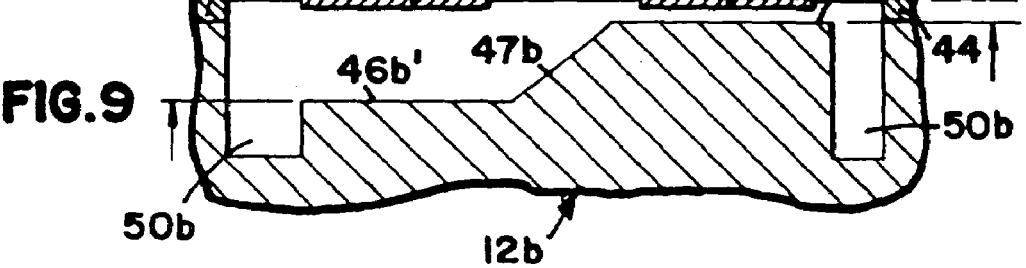
FIG. 9 is a view similar to FIG. 8 showing a second alternative embodiment of the present invention.

In the embodiment of FIG. 9, fluid is inclined to first flow onto step 46b before onto step 46b'. However, in FIG. 9, the volume barrier 50a' of FIG. 8 has been replaced with a ramp surface 47b connecting steps 46b and 46b'. Therefore, fluid can flow from space Sb to space Sb' after space Sb has first filled with fluid.

Figure 10:
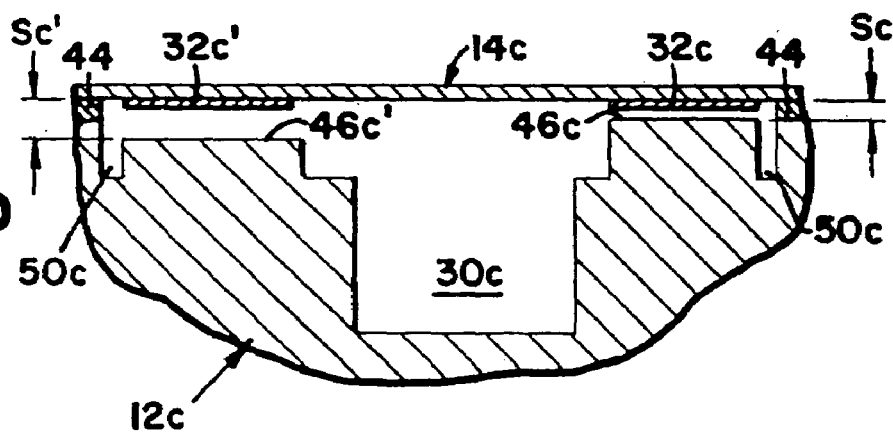
FIG. 10 is a view similar to those of FIGS. 8 and 9 showing a third alternative embodiment of the present invention.
Figure 15:
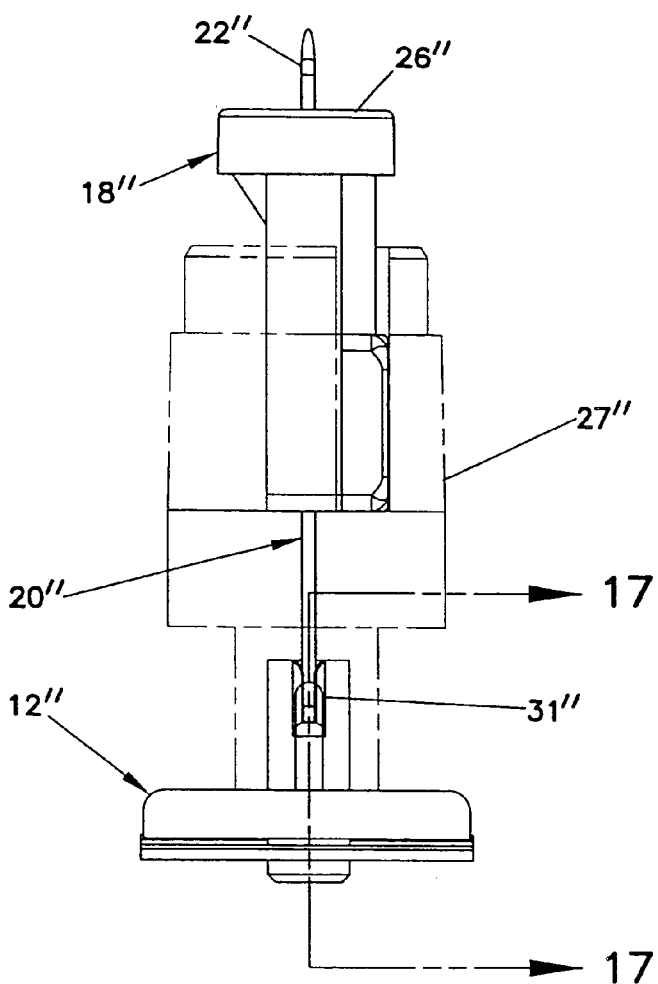
FIG. 15 is a rear end elevation view of the apparatus of FIG. 13.

In the embodiment of FIGS. 10 and 11, the steps 46c, 46c' are positioned on opposite sides of the reservoir 30c. If spaces Sc and Sc' are equal, fluid flows simultaneously into the spaces Sc and Sc' but does not flow between the spaces Sc and Sc'. The spaces Sc and Sc' may be varied to change the rate of flow into the spaces Sc and Sc'.

The embodiment of FIG. 12 is similar to that of FIG. 9. Instead of the ramp 47b of FIG. 9 (which connects steps 46b and 46b' directly across a side-to-side path), the ramp 47d is U-shaped for fluid to flow from step 46d to step 46d' in a U-shaped path A on a side of the steps 46d, 46d' opposite the reservoir 30d.

In FIGS. 1–6, the needle 20 is parallel to the plane of the capillary space 48 (as best illustrated in FIG. 4). FIGS. 13–17 illustrate an embodiment with the needle 20" perpendicular to a capillary space 48" (shown in FIGS. 16 and 17). In FIGS. 13–17, a plastic main body 12" includes a planar handle strip 13" and a perpendicular hollow hub 15" or peg extending from a first or bottom side 13a" of the strip 13". A bore 17" (FIGS. 16 and 17) extends trough the hub 15" and through the strip 13" to be exposed on a second or top side 13b" of the strip 13".

Figure 17:
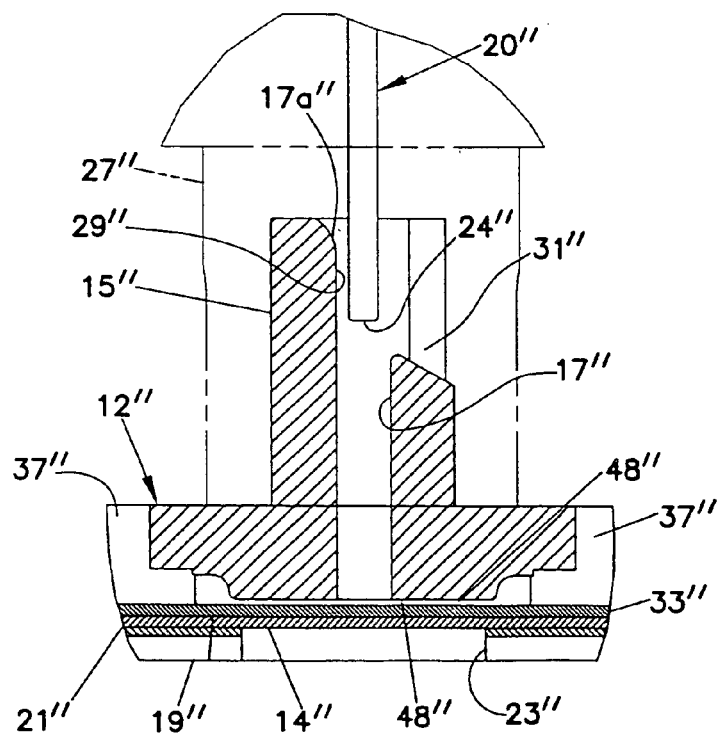
FIG. 17 is a view taken along line 17—17 in FIG. 15.
Figure 16:
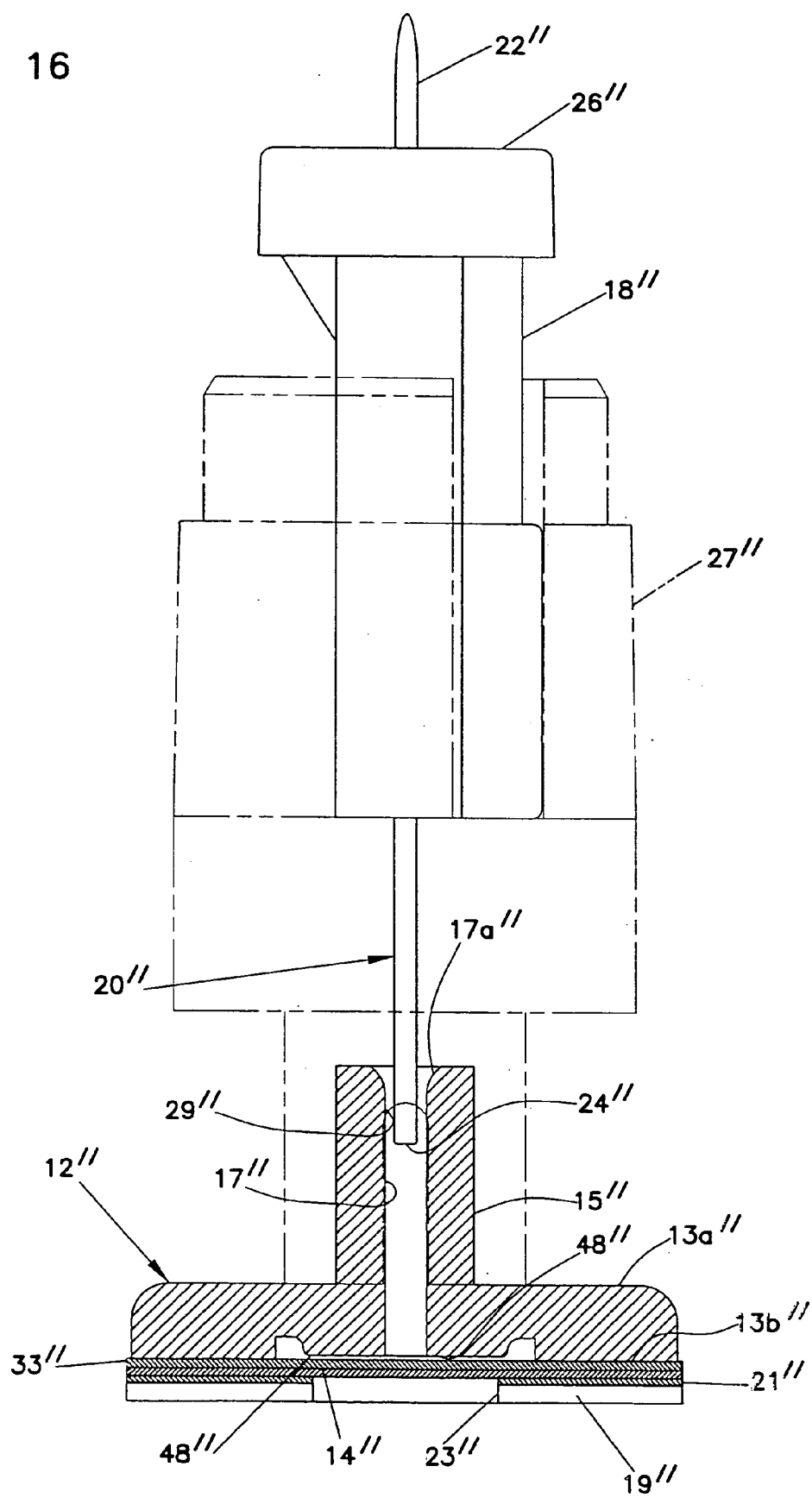
FIG. 16 is a view taken along line 16—16 in FIG. 14.

Best shown in FIGS. 16 and 17, a test membrane 14" is placed on the second side 13b" overlying the bore 17". A cover 19" is adhered to the test membrane 14" by an adhesive layer 21".

The main body 12" is sized to be placed in a monitor (not shown) with the test membrane 14" in alignment with test apparatus carried by the monitor. For example, the test membrane 14" is aligned with optic components for colormetric testing. In such an embodiment, the cover 19" has a hole 23" to expose the test membrane 14" overlying the bore 17". In alternative embodiments, the test membrane 14" can also be aligned with electrodes for electrochemical testing or with optic components for infrared testing.

The needle 20" is surrounded by a ferrule 18". The ferrule 18" hold the needle 20" with a distal tip 22" (i.e., a penetration end) extending from the ferrule 18". The needle 20" terminates at a discharge end 24" (numbered only in FIGS. 16 and 17). The penetration end 22" protrudes from a radially spaced ring end 26" of the ferrule 18". To enhance fluid collection, distal tip 22" is bent as is more fully described in commonly assigned U.S. Pat. No. 6,702,791. The ferrule 18" has a slot 25" to expose needle 20" so that adhesive can be applied to the needle 20" to adhere the needle 20" to the ferrule 18" during assembly.

Shown only in phantom lines in order to better illustrate internal features, an adapter 27" is provided to connect the ferrule 18" to the hub 15" with the needle 20" coaxially aligned with the bore 17". The discharge end 24" is positioned in the bore 17" near a distal end 17a" of the bore 17" (as shown in FIGS. 16 and 17). The needle 20" is a smaller diameter than the bore 17" to define an annular space 29" surrounding the discharge end 24". A vent opening 31" (shown in FIGS. 15 and 17) is formed through the cylindrical wall of the hub 15" at the distal end 17a" and in communication with the annular space 29".

The test membrane 14" is spaced from the second side 13b" of the strip 13" to define a capillary space 48" (shown in FIGS. 16 and 17) between the membrane 14" and the second side 13b". The capillary space 48" overlies the bore 17". Accordingly, as in previously described embodiments, fluid flows from the needle 20" through the discharge end 24" and into the bore 17" which acts as a collection well or reservoir as in the reservoir 30 of the previously described embodiment. When the bore 17" fills, the fluid contacts the capillary space 48" and is rapidly wicked into the capillary space 48" and absorbed into the test membrane 14". A porous wick material 33" (e.g., a porous polyester layer) fills the capillary space 48" to assist in uniform distribution of fluid onto the membrane 14".

Preferably (but not necessarily), the hub is hydrophobic. The surface tension of the fluid prevents the fluid from discharging through the narrow annual space 17" or vent hole 31". Vent holes 37" are formed through the strip 13" from the capillary space 48". When fluid is wicked from the collection well or bore 17" into the capillary space 48", the vent holes 37" permit air to escape from the capillary space 48". Simultaneously, the vent hole 31" permits a larger volume of air to enter the bore 17" so that the capillary wicking of the fluid is not acting against a vacuum. Vent hole 31" is optional since the annular space 17" also provides a venting opportunity utilizing air flow through spacing tolerances in the ferrule 18" and adapter 27". The adapter 27" may be provided with a vent slot 41" (FIG. 13) to admit air to vent 31" and space 17".

From the foregoing detailed description, the present invention has been described in a preferred embodiment. Modifications and equivalents of such disclosure are intended to be included in the appended claims. For example, either or both of the reservoir 30 and capillary test space 48 need not be an empty volume but could be filled with an absorbent material.

The claimed invention is:

1. An apparatus for collecting a body fluid for testing for an analyte contained within said body fluid, said apparatus comprising:
    a conduit having a first end for admitting a body fluid and transporting said body fluid from said first end to a discharge end of said conduit;
    a reservoir for receiving and collecting a flow of body fluid from said discharge end of said conduit, wherein said reservoir is defined by a hollow hub having a bore having a diameter greater than a diameter of said conduit;
    a test membrane; and
    a test space positioned substantially perpendicularly to said conduit and between said test membrane and said reservoir, said test space configured to be in contact with said fluid after said fluid has accumulated within said reservoir to a transfer volume of fluid, wherein said test space is sized to wick said fluid from said reservoir when said fluid in said reservoir attains said transfer volume.

2. The apparatus of claim 1 wherein said conduit is coaxially aligned within said bore.

3. The apparatus of claim 1 wherein said hollow hub comprises a vent hole.

4. The apparatus of claim 1 wherein said hollow hub comprises a hydrophobic material.

5. An apparatus for collecting a body fluid for testing for an analyte contained within said body fluid, said apparatus comprising:
    a conduit having a first end for admitting a body fluid and transporting said body fluid from said first end to a discharge end of said conduit;
    a reservoir for receiving and collecting a flow of body fluid from said discharge end of said conduit;
    a test membrane;
    a test space positioned substantially perpendicularly to said conduit and between said test membrane and said reservoir, said test space configured to be in contact with said fluid after said fluid has accumulated within said reservoir to a transfer volume of fluid, wherein said test space is sized to wick said fluid from said reservoir when said fluid in said reservoir attains said transfer volume;
    a porous material within said test space and overlying said test membrane.

6. An apparatus for collecting a body fluid for testing for an analyte contained within said body fluid, said apparatus comprising:
    a conduit having a first end for admitting a body fluid and transporting said body fluid from said first end to a discharge end of said conduit;
    a planar test body having a first surface and a second surface, wherein said planar test body comprises a test space positioned relative to a reservoir to be in contact with said fluid after said fluid has accumulated within said reservoir to a transfer volume of fluid, wherein said test space is sized to wick said fluid from said reservoir when said fluid in said reservoir attains said transfer volume; and
    a hub extending from said first surface and comprising a bore extending through said first surface, wherein said discharge end of said conduit is positioned coaxially within said bore wherein said reservoir is defined by said space within said bore not occupied by said discharge end of said conduit.

7. The apparatus of claim 6 wherein said planar test body further comprises:
    a test membrane positioned between said test space and said second surface; and
    an opening in said second surface wherein said test membrane is exposed therethrough for testing said fluid.

8. The apparatus of claim 6 wherein said planar test body further comprises a porous material positioned within said test space.

9. The apparatus of claim 6 wherein said planar test body further comprises a vent hole for venting said test space.

10. The apparatus of claim 6 wherein said planar test body further comprises components for testing said fluid, said components selected from electrodes for electrochemical testing and optical components for optical testing.

11. The apparatus of claim 6 wherein said hub extends substantially perpendicularly to said planar test body.

12. The apparatus of claim 6 wherein said hub comprises a vent hole for venting said reservoir.

* * * * *